United States Patent
Frazier et al.

(10) Patent No.: US 7,283,860 B2
(45) Date of Patent: Oct. 16, 2007

(54) COMMUNICATION SYSTEMS FOR USE WITH MAGNETIC RESONANCE IMAGING SYSTEMS

(75) Inventors: Michael Frazier, Lower Burrell, PA (US); Paul Reynolds, Harmony, PA (US); Alan Hirschman, Glenshaw, PA (US); John Gardner, Wexford, PA (US); Douglas Zatezalo, Allison Park, PA (US); Bruno Fazi, Pittsburgh, PA (US)

(73) Assignee: MEDRAD, Inc., Indianola, PA (US)

( * ) Notice: Subject to any disclaimer, the term of this patent is extended or adjusted under 35 U.S.C. 154(b) by 463 days.

(21) Appl. No.: 10/622,242

(22) Filed: Jul. 18, 2003

(65) Prior Publication Data

US 2004/0030233 A1 Feb. 12, 2004

Related U.S. Application Data

(62) Division of application No. 09/586,140, filed on Jun. 2, 2000, now Pat. No. 6,704,592.

(51) Int. Cl.
*A61B 5/05* (2006.01)

(52) U.S. Cl. ............ 600/410; 600/407; 600/420; 604/131

(58) Field of Classification Search ............ 600/420, 600/422, 407, 423, 431, 432
See application file for complete search history.

(56) References Cited

U.S. PATENT DOCUMENTS 3,523,523 A 8/1970 Reich et al.

(Continued)

FOREIGN PATENT DOCUMENTS

DE 44 40 619 8/1995

(Continued)

OTHER PUBLICATIONS

Nishiura, N., et al., "An Optical and RF Telemetry Drug Injection Control and ECG System For Awake Small Animal Studies," Proceedings of the Annual International Conference of the Engineering in Medicine and Biology Society, Orlando, FL, IEEE, vol. 13, Conf. 5, pp. 2162-2163 (1991).

(Continued)

*Primary Examiner*—Eleni Mantis Mercader
*Assistant Examiner*—James Kish
(74) *Attorney, Agent, or Firm*—James Stevenson Gregory Bradley

(57) ABSTRACT

An injector system for injection of a fluid medium into a patient within an electromagnetic isolation area. The injector system includes a powered injector, a system controller therefor, and a plurality of communication units. The powered injector is positioned within the isolation area. A first communication unit integral with the powered injector enables the first communication unit and the powered injector to be moved as a unit. The system controller is positioned outside the isolation area and has a second communication unit integral therewith. An intermediate communication unit ensures communication between the first and the second communication units and therethrough between the powered injector and the system controller using an authentication technique therewith. The first, second and intermediate communication units are adapted to communicate by transmission of radio frequency (RF) energy. The RF energy is chosen to avoid interfering with the operation of MRI scanners.

15 Claims, 7 Drawing Sheets

U.S. PATENT DOCUMENTS

| | | | |
|---|---|---|---|
| 3,812,843 A | | 5/1974 | Wootten et al. |
| 3,829,195 A | * | 8/1974 | Rawson ........................ 385/34 |
| 3,880,138 A | | 4/1975 | Wootten et al. |
| 3,888,239 A | | 6/1975 | Rubinstein |
| 4,006,736 A | | 2/1977 | Kranys et al. |
| 4,044,757 A | | 8/1977 | McWhorter et al. |
| 4,119,362 A | * | 10/1978 | Holzman ........................ 385/74 |
| 4,183,618 A | * | 1/1980 | Rush et al. ..................... 385/79 |
| 4,360,249 A | * | 11/1982 | Slemon ........................ 385/51 |
| 4,502,488 A | | 3/1985 | Degironimo et al. |
| 4,585,009 A | | 4/1986 | Barker et al. |
| 4,613,328 A | | 9/1986 | Boyd |
| 4,619,653 A | | 10/1986 | Fischell |
| 4,677,980 A | | 7/1987 | Reilly et al. |
| 4,695,271 A | | 9/1987 | Goethel |
| 4,737,712 A | * | 4/1988 | Stormont et al. ........... 324/307 |
| 4,840,620 A | | 6/1989 | Kobayashi et al. |
| 4,854,324 A | | 8/1989 | Hirschman et al. |
| 4,885,538 A | | 12/1989 | Hoenniger, III et al. |
| 4,981,137 A | | 1/1991 | Kondo et al. |
| 5,027,824 A | | 7/1991 | Dougherty et al. |
| 5,030,201 A | | 7/1991 | Palestrant |
| 5,134,373 A | | 7/1992 | Tsuruno et al. |
| 5,236,417 A | | 8/1993 | Wallis |
| 5,244,461 A | | 9/1993 | Derlien |
| 5,269,762 A | | 12/1993 | Armbruster et al. |
| 5,274,330 A | | 12/1993 | Rindlisbacher et al. |
| 5,300,031 A | | 4/1994 | Neer et al. |
| 5,342,298 A | | 8/1994 | Michaels et al. |
| 5,352,979 A | | 10/1994 | Conturo |
| 5,354,273 A | | 10/1994 | Hagen |
| 5,357,959 A | | 10/1994 | Fishman |
| 5,411,485 A | | 5/1995 | Tennican et al. |
| 5,417,213 A | | 5/1995 | Prince |
| 5,458,122 A | | 10/1995 | Hethuin |
| 5,464,014 A | | 11/1995 | Sugahara |
| 5,472,403 A | | 12/1995 | Cornacchia et al. |
| 5,494,036 A | * | 2/1996 | Uber et al. ................. 600/432 |
| 5,862,803 A | | 1/1999 | Besson et al. |
| 5,994,984 A | | 11/1999 | Stancil et al. |
| RE36,648 E | | 4/2000 | Uber, III et al. |
| 6,198,285 B1 | * | 3/2001 | Kormos et al. ............. 324/318 |
| RE37,602 E | | 3/2002 | Uber, III et al. |

FOREIGN PATENT DOCUMENTS

| | | |
|---|---|---|
| DE | 196 21 393 | 12/1997 |
| EP | 0 105 550 | 4/1984 |
| EP | 0 495 287 | 7/1992 |
| EP | 0 518 100 | 12/1992 |
| EP | 0 655 220 | 5/1995 |
| JP | 61-155846 | 7/1986 |
| JP | 1-223943 | 9/1989 |
| JP | 1-165010 | 11/1989 |
| JP | 1-303139 | 12/1989 |
| JP | 5-84296 | 4/1993 |
| JP | 7-178169 | 7/1995 |
| JP | 2752909 | 2/1998 |
| WO | WO99/27847 | 6/1999 |
| WO | WO 01/92907 | 12/2001 |

OTHER PUBLICATIONS

"Market Scan," Diagnostic Imaging, p. 61 (Sep. 1988).
Injectron MRT Brochure, Medtron MR-Injector, Technical Data (date unknown).
CT/MR Injector Brochure, Ulrich GmbH & Co. KG, (Nov. 1999).
Mildenberger, A., "MR Jet Basic Configuration DM 29000," Automation GmbH (Feb. 11, 1998).
Saini, S., et al., "In Vitro Evaluation of a Mechanical Injector for Infusion of Magnetic Resonance Contrast Media," Technical Report, Investigative Radiology, vol. 26, No. 8, pp. 748-751 (Aug. 1991).
Angioject 3 Brochure, CGR, Paris, France (1975).
Mallinckrodt, Optistar MR Contrast Delivery System Brochure, OR00200 (Feb. 2000).
International Search Report for Counterpart PCT Application PCT/US01/40826.
"Medrad Targets Market for MRI," Allison Hargraves, Pittsburgh Business Times, vol. 7, No. 18, p. 1(2) (Dec. 21, 1987).
"Detection of Acute Avascular Necrosis of the Femoral Head in Dogs: Dynamic Contrast-Enhanced MR Imaging vs. Spin-Echo and STIR Sequences," AJR: 159, pp. 1255-1261, Dec. 1992.
"An Infusion Pump That Works in MRI," Anesth. Analg. 1993: 77, p. 645, Letters to the Editor.
Mallinckrodt Optistar MR Digital Injection System, Operator's Manual, 801900-A (Nov. 1999).
Mallinckrodt Optistar MR Digital Injection System, Service and Parts Manual, 801902-A (Apr. 2000).
Medrad Spectris MR Injection System Service Manual, Catalog No. SSM200 1, 92901-T-129, Rev. A (1996).
Medrad Spectris MR Injector Operation Manual, SOM 200E, 92901-T-107, Rev. E (1996).
Invivo Research, Inc., Millennia 3155 MVS Monitor Operations Manual, IRI PN #9545, Release 3,(Mar. 1998).
Invivo Research Inc., Omni-Trak 3150 MRI Patient Monitor Operations Manual, (Jan. 1998).
Injektron 82 MRT User Instructions, Version MR2, pp. 5, 30 and 31, (Mar. 10, 1999).

* cited by examiner

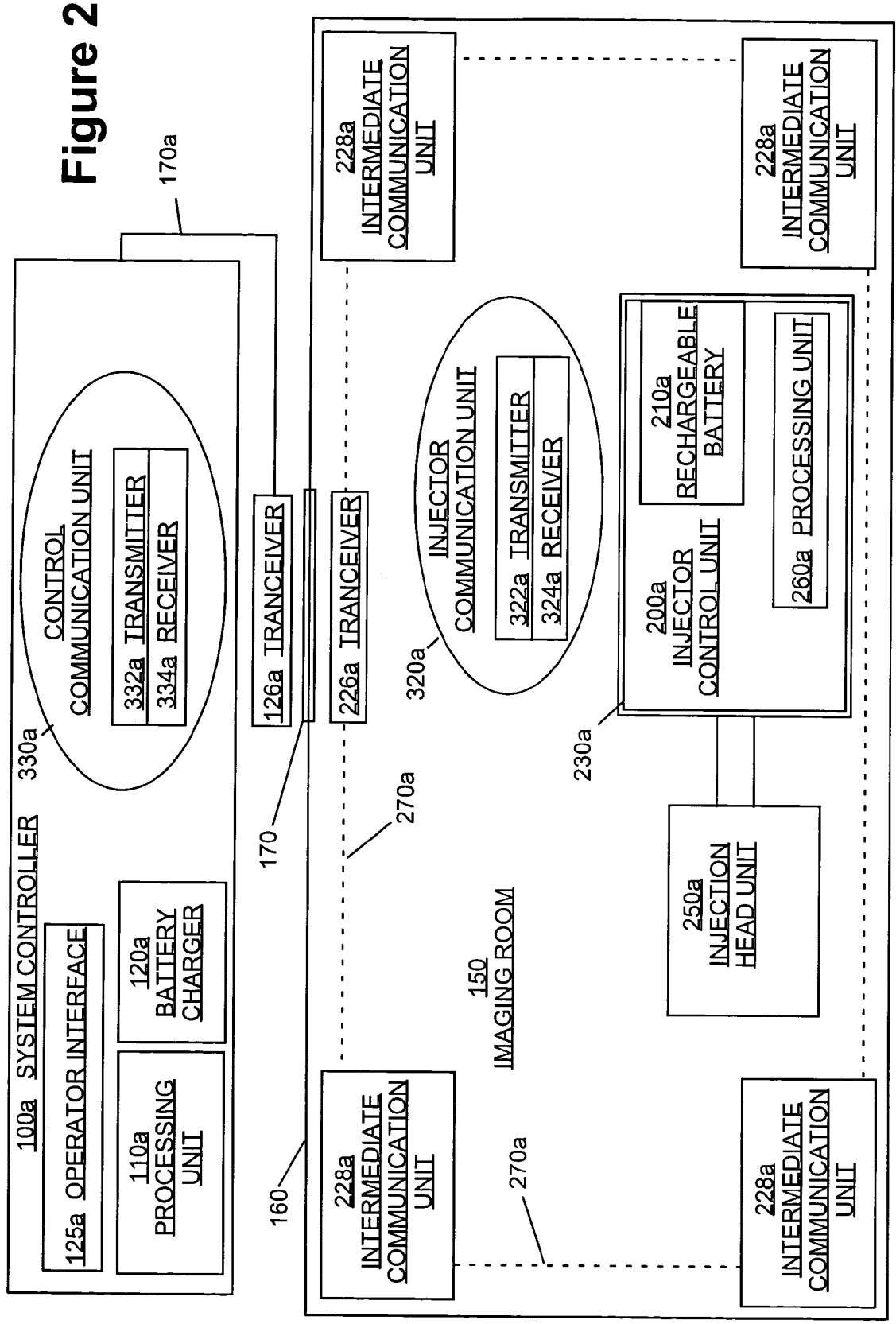

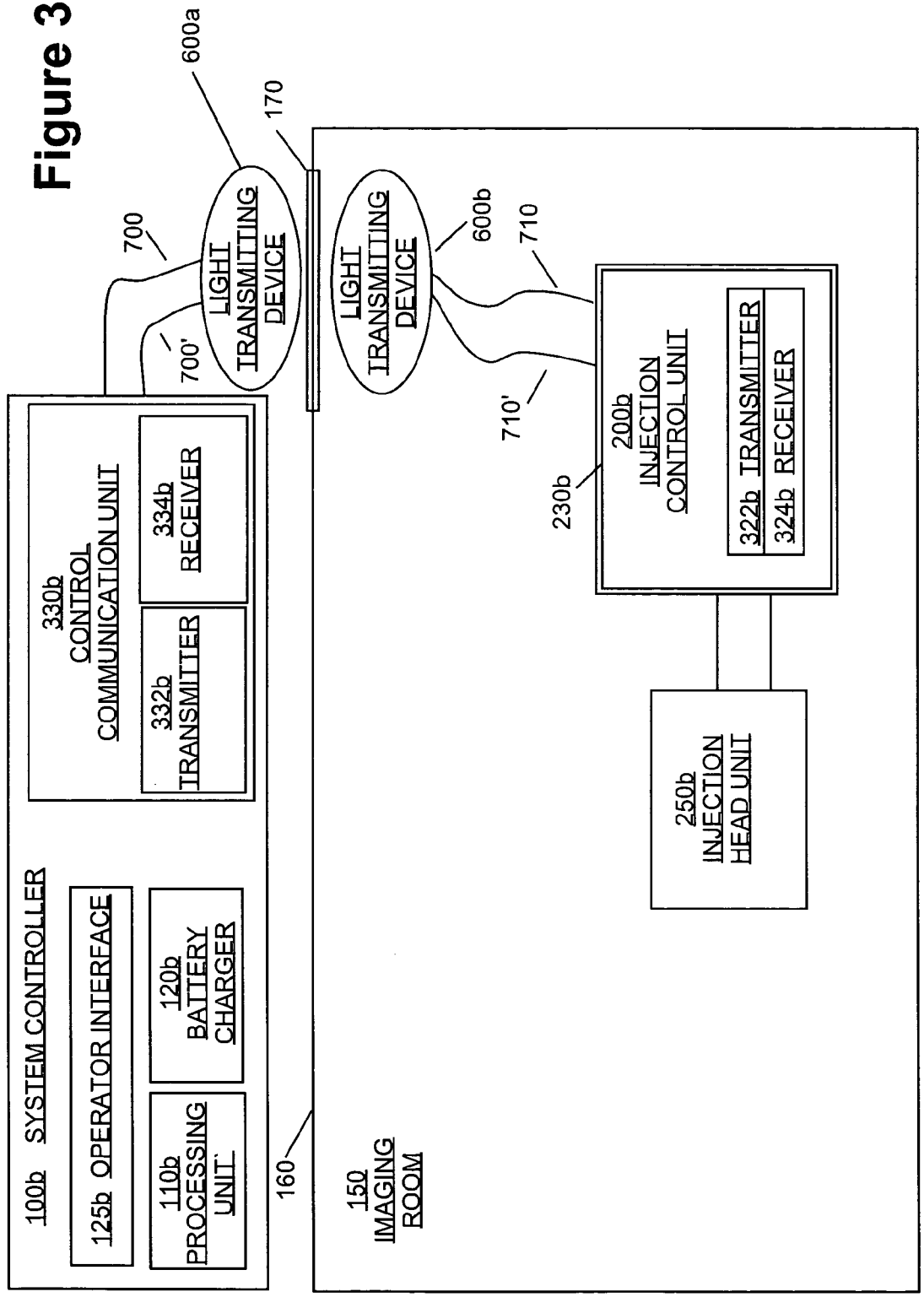

COMMUNICATION SYSTEMS FOR USE WITH MAGNETIC RESONANCE IMAGING SYSTEMS

CROSS-REFERENCE TO RELATED APPLICATION

This application is a division of application Ser. No. 09/586,140, filed on Jun. 2, 2000 now U.S. Pat. No. 6,704,592, the contents of which are incorporated herein by reference.

BACKGROUND OF THE INVENTION

The present invention relates generally to communication systems and methods of communication, and, especially, to communication systems and methods of communication for use in magnetic resonance imaging procedures.

In general, magnetic resonance imaging (MRI) systems require isolation from external sources of electromagnetic fields to optimize image quality. Conventional MRI systems, therefore, typically include some form of electromagnetic isolation shield or barrier. Most often, a room enclosed by copper sheeting or conductive mesh material isolates or shields the imaging system from undesirable sources of electromagnetic radiation, including the electromagnetic noise inherent in the atmosphere.

A number of powered injectors for use in MRI have been developed. These powered injectors are a potential source of electromagnetic radiation. To realize the full benefit of "shielded" rooms in MRI, injector systems typically employ a controller that is isolated from the powered injector. For example, the controller may be placed outside of a shielded room (e.g., in the MRI control room) in which the MRI scanner and the powered injector operate. Such isolation prevents undesirable electromagnetic radiation generated by the injector system controller from interfering with the signals used to create the magnetic resonance images.

The external, isolated location of the system controller creates various problems associated with the installation and operation of these systems. One such problem is the need to provide a communication link between the external controller and the injector (which is located within the shielded area), without introducing extraneous electromagnetic radiation. In other words, there is a need to provide injector control circuitry while maintaining the integrity of the electromagnetic shield.

Previous attempts to solve these problems included drilling holes in the wall of the electromagnetic shield for inserting the necessary lines or, alternatively, laying the lines under a shielded floor of the imaging room. These alternatives have proven to be less than optimum, since spurious radiation can arise from the presence of the various supply cables within the shielded imaging suite. Additionally, MRI systems, which employ these alternatives often, require substantial site dedication and are, therefore, not very portable.

U.S. Pat. No. 5,494,036, the disclosure of which is incorporated herein by reference, discloses, in one embodiment, an improved communication link that is made through a window in an isolation room barrier. These windows are typically in the form of a glass laminate containing a conductive wire mesh, or alternatively, a window that is coated with a thin sheet of conductive material such as gold to maintain the shielding characteristics of the isolation area or room.

The above-noted embodiment of the communications link of U.S. Pat. No. 5,494,036 includes electromagnetic transceivers that operate in a frequency range which permeates the window while maintaining the integrity of the isolation barrier. The internal transceiver is positioned on the window and is tethered or attached to the injector control in the MRI shielded room via a communication line. The external transceiver is positioned on the opposite side of the window (i.e., in the MRI control room) and is connected to the injector system controller. Infrared or electromagnetic energy in the visual range are noted to provide the best results. A fiber optic communication link is also disclosed.

Although improvements have been made in communication systems for use in magnetic resonance imaging, it remains desirable to develop improved communication systems.

SUMMARY OF THE INVENTION

In one aspect, the present invention provides a system for bi-directional communication during a magnetic resonance imaging procedure using an MRI scanner and an electromagnetic isolation barrier defining an isolation area within which the scanner is positioned.

The system includes generally at least a first source of RF signals outside the frequency range of the scanner and at least a first receiver for RF signals outside the frequency range of the scanner. The first source of RF signals and the first receiver of RF signals are in communication with a system controller positioned outside the isolation area. The system also includes at least a second source of RF signals outside the frequency range of the scanner and at least a second receiver for RF signals outside the frequency range of the scanner. The second source of RF signals and the second receiver for RF signals are positioned within the isolation area.

The system of the present invention allows bi-directional communication with and control of instrumentations within the isolation barrier from the system controller located outside of the isolation barrier. Preferably, the frequency of the RF signal is above approximately 1 Gigahertz. For example, the RF signal can be in the 2.4 GHz frequency range.

The system can, for example, include a powered injector to inject a fluid medium into a patient. In this embodiment, the second receiver and the second source are preferably in communicative connection with a control unit of the powered injector. The second receiver and the second source can, for example, be connected to the injector control unit so that the injector control unit, the second receiver and the second source can be moved as a unit.

In another aspect, the present invention provides an injector system for injection of a fluid medium into a patient within an electromagnetic isolation area. The injector system includes a powered injector positioned within the isolation area and a system controller positioned outside the isolation area. The system controller includes an operator interface. The powered injector includes a first communication unit, and the system controller includes a second communication unit. The first communication unit and the powered injector are connected so that the first communication unit and the powered injector can be moved as a unit. The first communication unit is also adapted to communicate with the second communication unit by transmission of energy through the air. The energy is chosen to not create substantial interference with a magnetic resonance imaging scanner positioned within the isolation area.

The energy can be electromagnetic energy outside the frequency range of the scanner (for example, RF energy above approximately 1 Gigahertz). The energy can also be vibrational energy, sonic energy or ultrasonic energy. Furthermore, the energy can be visible light or infrared light.

The injector system can further include at least one intermediate communication unit positioned within the isolation area through which the first communication unit can communicate with the second communication unit. The first communication unit communicates with the intermediate communication by transmission of energy through the air. A plurality of such intermediate communication units can be positioned within the isolation area to facilitate communication.

In another aspect, the present invention provides a system for use in an MRI procedure that includes an MRI scanner positioned on a first side of an electromagnetic isolation barrier and an injector control unit to control injection of a fluid medium into a patient. The injector control unit is also positioned on the first side of the isolation barrier. The system also includes a system controller positioned on a second side of the isolation barrier. The injector control unit includes a first communication unit, and the system controller includes a second communication unit. The first communication unit is adapted to communicate with the second communication unit in a bi-directional manner by transmission of energy through the air. As described above, the energy is chosen to not create substantial interference with a magnetic resonance imaging scanner.

The present invention also provides a communication system for use in an MRI procedure that includes a first communication unit positioned within a shielded housing on an interior side of the isolation barrier. The first communication unit includes a first receiver and a first transmitter. The communication system also includes a second communication unit positioned on an exterior side of the isolation barrier. The second communication unit includes a second receiver and a second transmitter. The first communication unit is in connection via optical cabling with a first light transmitting device positioned on an interior side of the isolation barrier adjacent a viewing window in the isolation barrier. The second communication unit is in connection via optical cabling with a second light transmitting device positioned on the exterior side of the isolation barrier adjacent a viewing window in the isolation barrier. The first communication unit and the second communication unit communicate via transmission of optical energy between the first light transmitting device and the second light transmitting device.

In one aspect, the first communication unit is positioned within a shielded housing of an injector control unit. The first light transmitting device can include a first lens assembly in communication with the first transmitter via optical cable and a second lens assembly in communication with the first receiver via optical cable. Likewise, the second light transmitting device can include a third lens assembly in communication with the second receiver via optical cable and a fourth lens assembly in communication with the second transmitter via optical cable. The first lens assembly and the third lens assembly are preferably in general alignment to enable communication between the first transmitter and the second receiver via transmission of light therebetween. Similarly, the second lens assembly and the fourth lens assembly are preferably in general alignment to enable communication between the first receiver and the second transmitter via transmission of light therebetween.

In another aspect, the present invention provides a method of controlling an injector within an isolation barrier of a magnetic resonance imaging area, including the steps of: transmitting RF signals outside the frequency range of the magnetic resonance imaging scanner from a system control unit positioned outside the isolation barrier to an injector control unit positioned inside the isolation barrier, the system control unit including an operator interface; and transmitting RF signals outside the frequency range of the magnetic resonance imaging scanner from the injector control unit to the system control unit.

The present invention also provides a method of transmitting data between the exterior of an isolation barrier of a magnetic resonance imaging area and the interior of the isolation barrier, including the steps of: positioning a first passive light transmitting assembly adjacent a translucent window in the isolation barrier on the outside of the isolation barrier; positioning a second passive light transmitting assembly adjacent the window on the interior of the isolation barrier in general alignment with the first light transmitting assembly such that light energy can be transmitted therebetween, and connecting the second light transmitting assembly via optical cable to a communication unit positioned within a shielded housing within the isolation barrier.

Numerous other objects and advantages of the present invention will be apparent from the following drawings and detailed description of the invention and its preferred embodiments.

BRIEF DESCRIPTION OF THE DRAWINGS

FIG. 2 illustrates another embodiment of a communication system of the present invention.

FIG. 3A schematically illustrates an embodiment of an MRI communication system including passive optical communication through the viewing window of an MRI room to a communication unit positioned within a shielded housing of an injection control unit.

DETAILED DESCRIPTION OF THE INVENTION

Figure 1A:
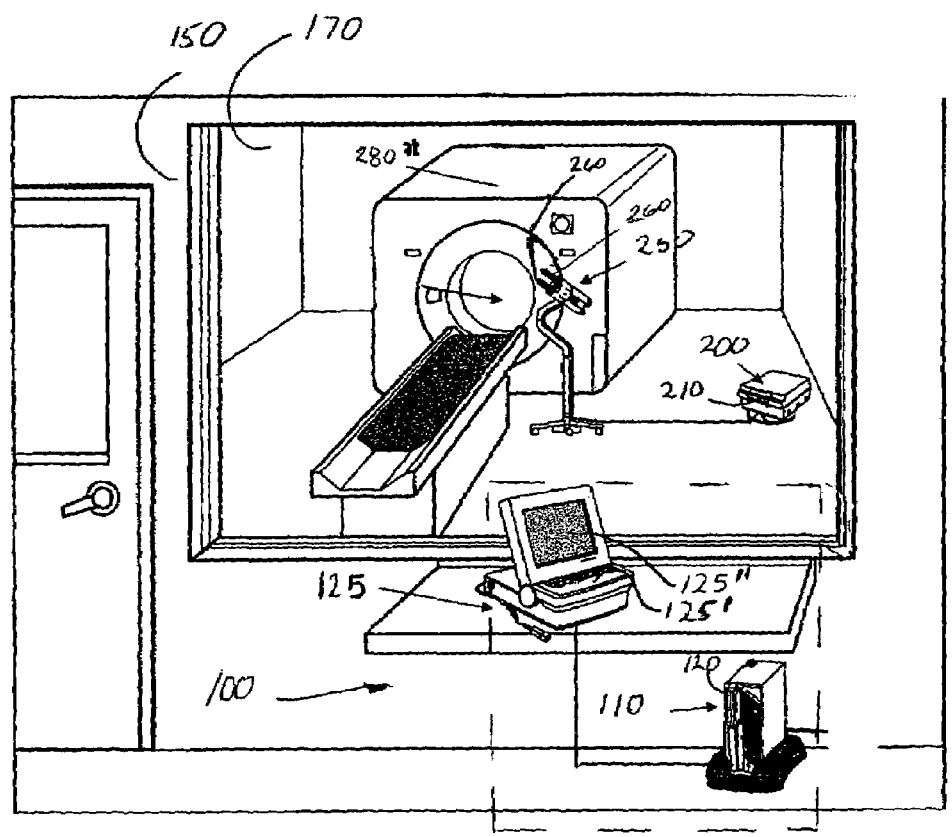
FIG. 1A illustrates a perspective view of one embodiment of a injection/communication system of the present invention.
Figure 1B:
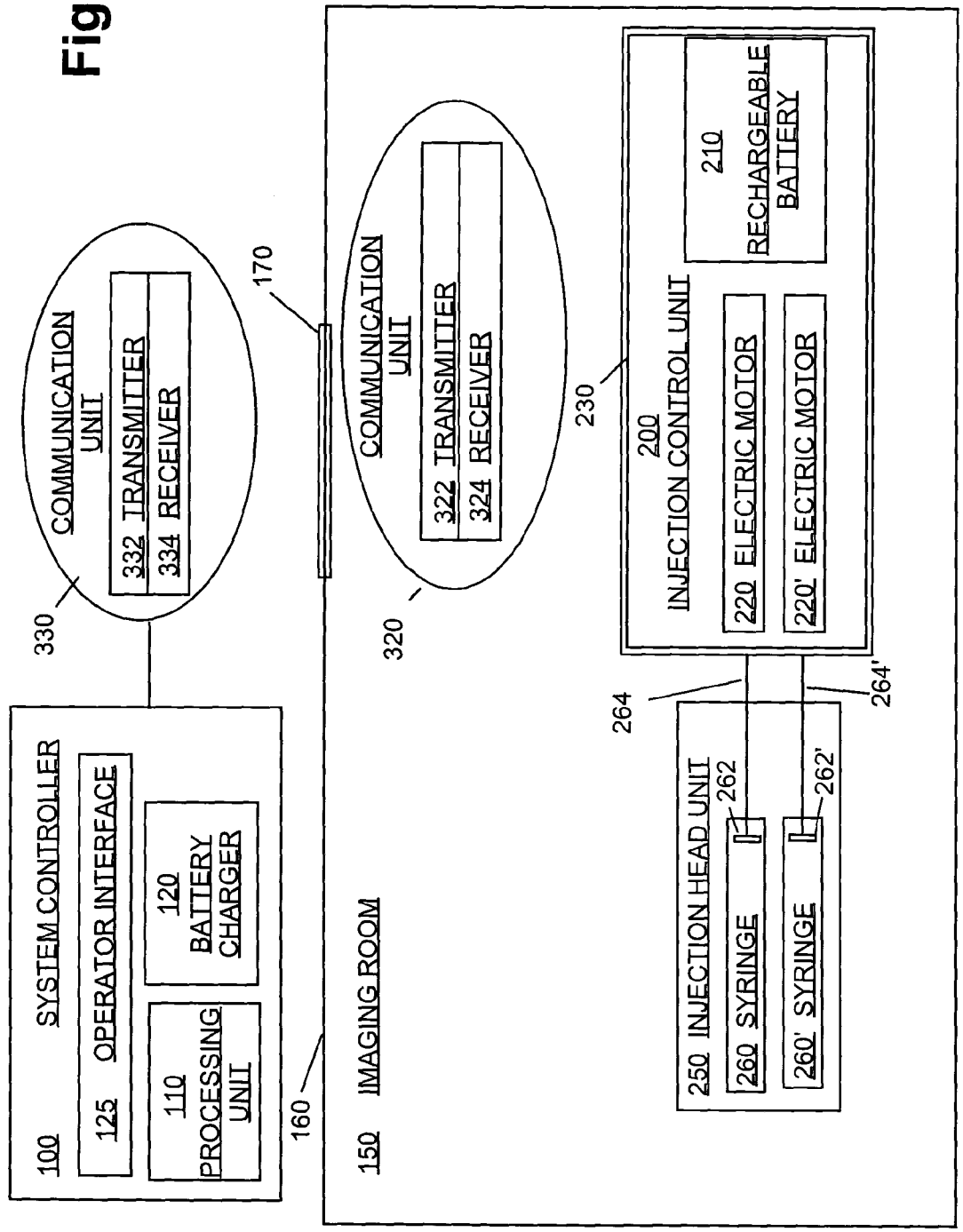
FIG. 1B schematically illustrates the communication system of FIG. 1A.

FIGS. 1A and 1B illustrate an embodiment of a magnetic resonance imaging system of the present invention. The MRI system preferably includes an external system controller 100 that preferably includes a processing unit 110 (for example, a digital microcomputer), a battery charger 120 and an operator interface 125 (including, for example a data entry unit 125' and a display 125"). System controller 100 is located outside of a shielded area such as an imaging room 150 that is shielded from electromagnetic interference by, for example, a shield 160 (see FIG. 1B). Electromagnetic isolation can, for example, be achieved by completely enclosing the room with copper sheet material or some other suitable, conductive layer such as wire mesh.

Shielded imaging room 150 preferably includes a patient viewing window 170 in shield 160 to allow an observer and/or operator to view the room without breaching electromagnetic shield 160. Window 170 can, for example, be formed by sandwiching a wire mesh material (not shown) between sheets of glass or by coating the window with a thin coating of conductive material such as gold (not shown) to maintain the continuity of electromagnetic shield 160.

The magnetic resonance imaging system also preferably includes a contrast media injection control unit 200 located within shielded imaging room 150. Injection control unit 200 is preferably powered by a rechargeable battery 210. Injection control unit 200 preferably includes control circuitry which controls electric motors 220 and 220', which are preferably located within injection control unit 200. Injection control unit 200 is preferably contained within an electromagnetic shield 230 to reduce or eliminate any undesired electromagnetic radiation generated by electric motors 220 and 220' from interfering with the magnetic field used to generate the magnetic resonance image.

Separation of the electric motors from the injection head 250, as well as the additional electromagnetic shielding, results in improved system performance and improved overall image quality. Injection control unit 200 can be separated (for example, by ten to fifteen feet) from injection head unit 250, which is typically placed near the patient. Although injection control unit 200 is preferably shielded to prevent RF interference, ferromagnetic material in injection control unit 200 can result in injection control unit 200 being drawn into magnet gantry 280. This undesirable result can result in damage to magnetic gantry 280, damage to injection control unit 200 and/or injury to personnel present in shielded room 150.

Injection head unit 250 is preferably located in close proximity to the patient to decrease the distance that the contrast media fluid must travel from the contrast media from syringes 260 and 260' connected to injection head unit 250. Injection head unit 250 further includes drive members 262 and 262' such as pistons that act to pressurize the contents of syringes 260 and 260', respectively, for injection into the patient. Drive members 262 and 262' are preferably connected to electric motors 220 and 220', respectively, in injection control unit 200 by a non-rigid connection such as by flexible mechanical drive shafts 264 and 264', respectively. Drive shafts 264 and 264' are preferably made from a nonferrous metal such as hard brass.

Figure 1C:
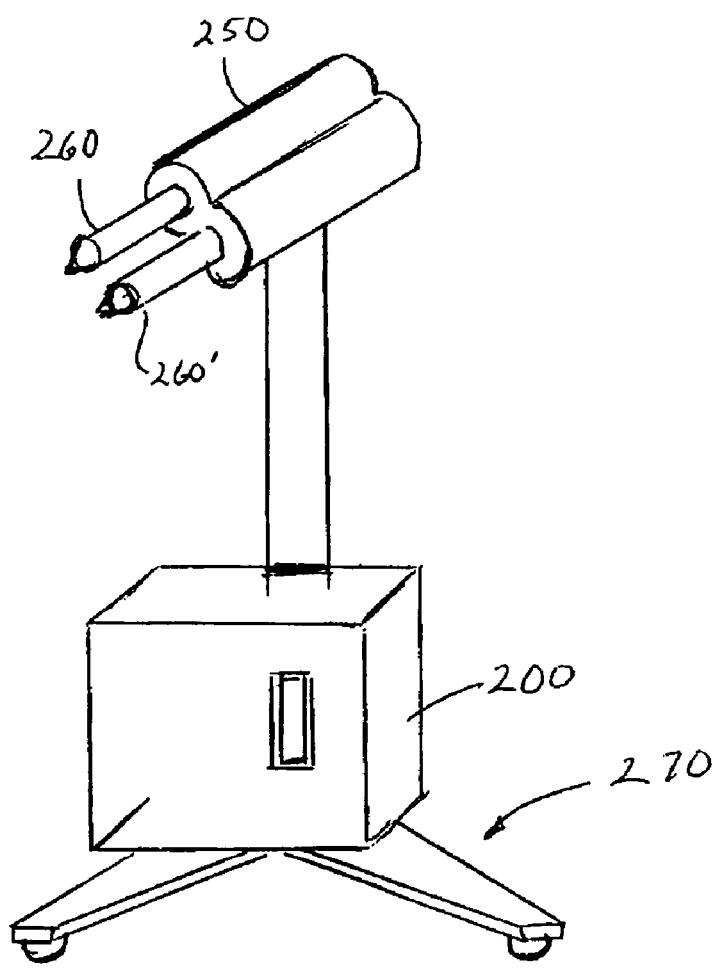
FIG. 1C illustrates a perspective view of an embodiment of an injector and an injector control unit mounted in a single mobile base unit.

As illustrated in FIG. 1C, injection control unit 200 can also be part of or mounted on the same mobile base unit 270 as injection head unit 250. In this embodiment, particular care is preferably take to limit the amount of ferromagnetic material used in injection control unit 200 to prevent mobile base 270 from being drawn into magnet gantry 280.

For control of injection head unit 250 by system controller 100, communication must be maintained between system controller 100 and injection control unit 200. In one aspect of the present invention, injector control unit 200 is preferably in communication with a communication unit 320 that preferably includes a transmitter 322 and a receiver 324. Likewise, control system 100 is preferably in communication with a communication unit 330. Communication unit 330 preferably includes a transmitter 332 and a receiver 334. Transmitters and receivers for use in the present invention can also be combined in transceivers as known in the art.

In one aspect of the present invention, transmitter 322 and receiver 324 of communication unit 320 are in wireless or cableless communication with communication unit 330. For example, there is preferably no communication line (for example, fiber optic cabling or shielded electrical cabling) connecting injector control unit 250 to a generally stationary communication device positioned at window 170.

Wireless communication (or communication through air) at any communication point between injection control unit 200 and system controller 100 within shielded room 170 can increase mobility of injection control unit 200, injection head unit 250 and/or personnel within room 170 by decreasing the amount of wiring in room 170. Communication unit 320 can, for example, be transportable/movable with mobile base 270. Injector head unit 250 and injector control unit 200 are thus "untethered" and can be relatively freely moved to different positions within the shielded area. This increased mobility facilitates use thereof by, for example, facilitating positioning of injector head unit 250. Moreover, eliminating communication lines on the floor of imaging room 150 may eliminate a potential source of tripping accidents in the shielded area.

In one embodiment, digital radio frequency (RF) energy that is outside the frequency range of the MRI scanner is used to transmit information to and/or from injector control unit 200. The imaging frequency of a 0.2 Tesla to 1.5 Tesla MRI scanner is typically in the range of approximately 8 MHz (Megahertz) to 64 MHz. A two-Tesla system may operate at an imaging frequency of up to approximately 85 MHz. The communication system of the present invention, therefore, transmits and/or receives RF signals that are preferably above approximately 100 MHz. More preferably, the RF signals are above approximately 400 MHz. Most preferably, the RF signals are above approximately 1 GHz (Gigahertz). In that regard, RF signals outside of the imaging frequency of the MRI scanner can be transmitted through "leaks" or intentional RF gaps that act as leaks (for example, tuned ports of ventilation ports) in isolation shield 160 without creating substantial interference with the imaging procedure. The ability of current isolation barriers to block RF signals is typically substantially reduced at frequencies above approximately 1 GHz, making RF signals above that frequency particularly suited for transmission through such isolation barriers without substantial loss of signal or interference with scanner 300.

Figure 1D:
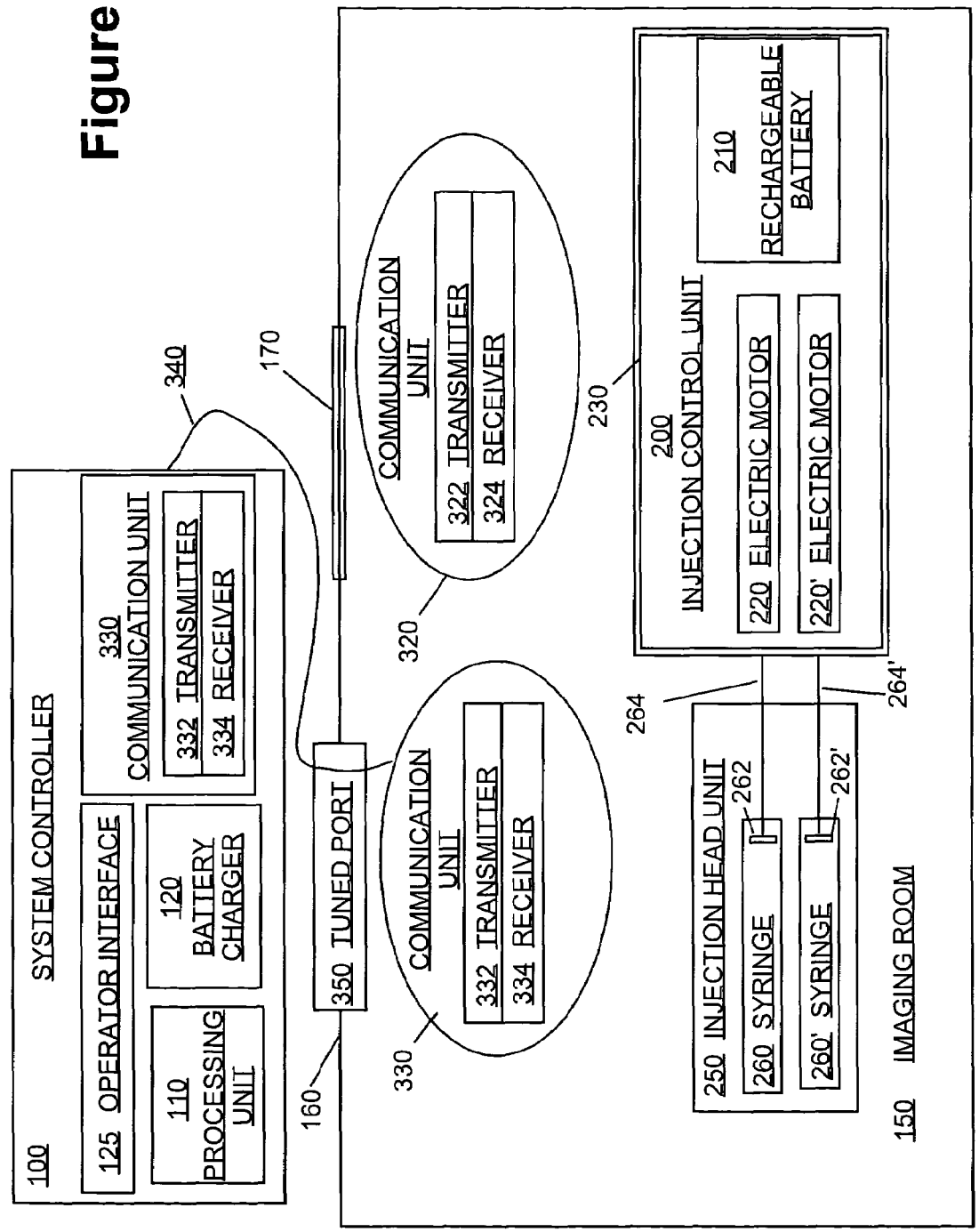
FIG. 1D schematically illustrates an alternative embodiment of the communication system of FIGS. 1A and 1B.

FIG. 1D illustrates an alternative embodiment of the present invention. In the embodiment of FIGS. 1A and 1B, RF communication unit 330 (including, for example, transmitter 332 and receiver 334) is positioned outside of imaging room 150. In the embodiment of FIG. 1D, RF communication unit 330 is positioned within imaging room 150 and is connected to system controller 100 via non-RF-interfering cabling 340 (for example, fiber optic cabling or shielded cabling) through tuned port 350. As used herein and commonly in the MR arts, the term "tuned port" prefers to an opening or aperture in shield 160 that is designed/dimensioned to prevent transmission of energy of certain frequencies therethrough. Communication unit 330 communicates with RF communication unit 320 as described above.

In one aspect, the radio frequency energy used in the communications system of the present invention is in the range of approximately 2.4 to 2.48 GHz, which is a band of energy set aside by the Federal Communication Commission and other national organizations for industry, scientific and medical (ISM) use. Operation in the 2.4 GHz ISM band allows license-free use and worldwide compliance.

Because many other communications systems may use RF signals in the range of frequencies used in the present invention, it may be desirable to modulate the signal between injector control unit 200 and system controller 100 to reduce or eliminate the potential for interference with or from such other communication systems. For example, frequency hopping spread spectrum modulation or direct sequencing spread spectrum modulation as known in the art may be used in the present invention. A detailed description of modulated transmissions is provided in WIT2410 2.4 GHZ Spread Spectrum Wireless Industrial Transceiver Integration Guide (Jun. 15, 1999) available from Digital Wireless Corporation of Norcross, Ga., the disclosure of which is incorporated herein by reference. Spread spectrum modulation is currently used at 900 MHz and 2.4 GHz.

However, even modulation techniques such as frequency hopping spread spectrum modulation or direct sequencing spread spectrum modulation are commonly use in RF communication devices, and the risk of interference with or from other devices may still be unacceptably high. Therefore, one or more unique data authentication techniques can be used for RF communication in the present invention. For example, at least a part of a communication sequence signal may be transmitted at two or more different RF frequencies (all of which are outside of the frequency range of the MRI scanner). For example, data can be transmitted at 2.4 GHz and 5.8 GHz simultaneously.

In general, any number of communication protocols or specifications can be used in digital RF transmission under the present invention. For example, the Bluetooth™ Technology of the Bluetooth Special Interest Group as set forth in the Bluetooth Specification Release 1.0 (the disclosure of which is incorporated herein by reference) is suitable for use in the present invention. The Bluetooth specification specifies a system solution comprising hardware, software and interoperability requirements and operates in the common 2.4 GHz ISM band.

Furthermore, any type(s) of energy that reduce or eliminate interference with the magnetic field used by the MRI scanner to generate an image are suitable for transmission of information in the present invention within the isolation barrier. For example, in addition to RF and other electromagnetic energy outside the frequency used by scanner 300 (for example, light energy (such as, visible light and/or infrared light), sonic energy, ultrasonic energy, and/or vibrational energy can be used.

In FIG. 2, injector control unit 200a includes a communication unit 320a that preferably includes a transmitter 322a and a receiver 324a. Likewise, system controller 100a includes a communication unit 330a. Communication unit 330a includes a transmitter 332a and a receiver 334a. As described above, the transmitter/receiver pairings can be in the form of transceivers.

In one embodiment, optical and/or infrared light is used to transmit information between system controller 100a and injector control unit 200a through, for example, window 170. In the case that optical/infrared light is used for a transmission signal, communication can be interrupted if there is not a direct "line of sight" between control communication unit 330a and injector communication unit 320a. To assist in providing a substantially direct line of sight, an optical/infrared transceiver 126a in communication with control communication unit 330a can, for example, be positioned at the outside of window 170 to transmit/receive optical/infrared signals through window 170. Signals to or from transceiver 126a can be transmitted directly from or to injector communication unit 320a. To further assist in providing a substantially direct line of communication, an optical/infrared transceiver 226a may also be positioned on the interior of window 170 to transmit to and receive signals from injector communication unit 320a. Furthermore, one or more intermediate/redirecting communication units 228a can be positioned at various locations about the shielded area. Intermediate communication units 228a may, for example, be adapted to redirect/relay signals between, for example, transceiver 226a and injector communication unit 320a. In this manner, injector control unit 200a can be moved freely about the shielded area without losing a communication link with system controller 100a.

Transceivers 226a and 126a and/or intermediate communication unit(s) 228a may also amplify or otherwise modify signals. For example, the signals between transceiver 126a and 226a may be in the form of light energy, ultrasonic energy, or vibrational energy. Transceiver 226a or intermediate communication unit(s) 228a may transform such signals into RF signals of an appropriate frequency (as described above) for communication with injector communication unit 320a. Transceiver 226a and redirecting communication unit(s) 228a can be physically linked as represented by communication lines 270a in FIG. 2. Likewise, control communication unit 330a and transceiver 126a can be connected by communication line(s) 170a. In this embodiment, like the embodiment of FIGS. 1A through 1D, communication unit 320a preferably remains untethered by any communication line.

In other embodiments, sonic and/or ultrasonic energy may, for example, be used to transmit information to and/or from communication unit 320a. Transceiver 226a and/or redirecting communications units 228a may, for example, transmit voice commands to communication unit 320a that may be interpreted by a processing unit 260a in communication connection with communication unit 320a for control of injector control unit 200a.

In general, any type of energy that may be used to transmit information through the air to and/or from communication unit 320a and/or communication unit 330a and that does not substantially interfere with the MRI scanner (that is, create unacceptable artifacts on an image) is suitable for use in the present invention.

Figure 3B:
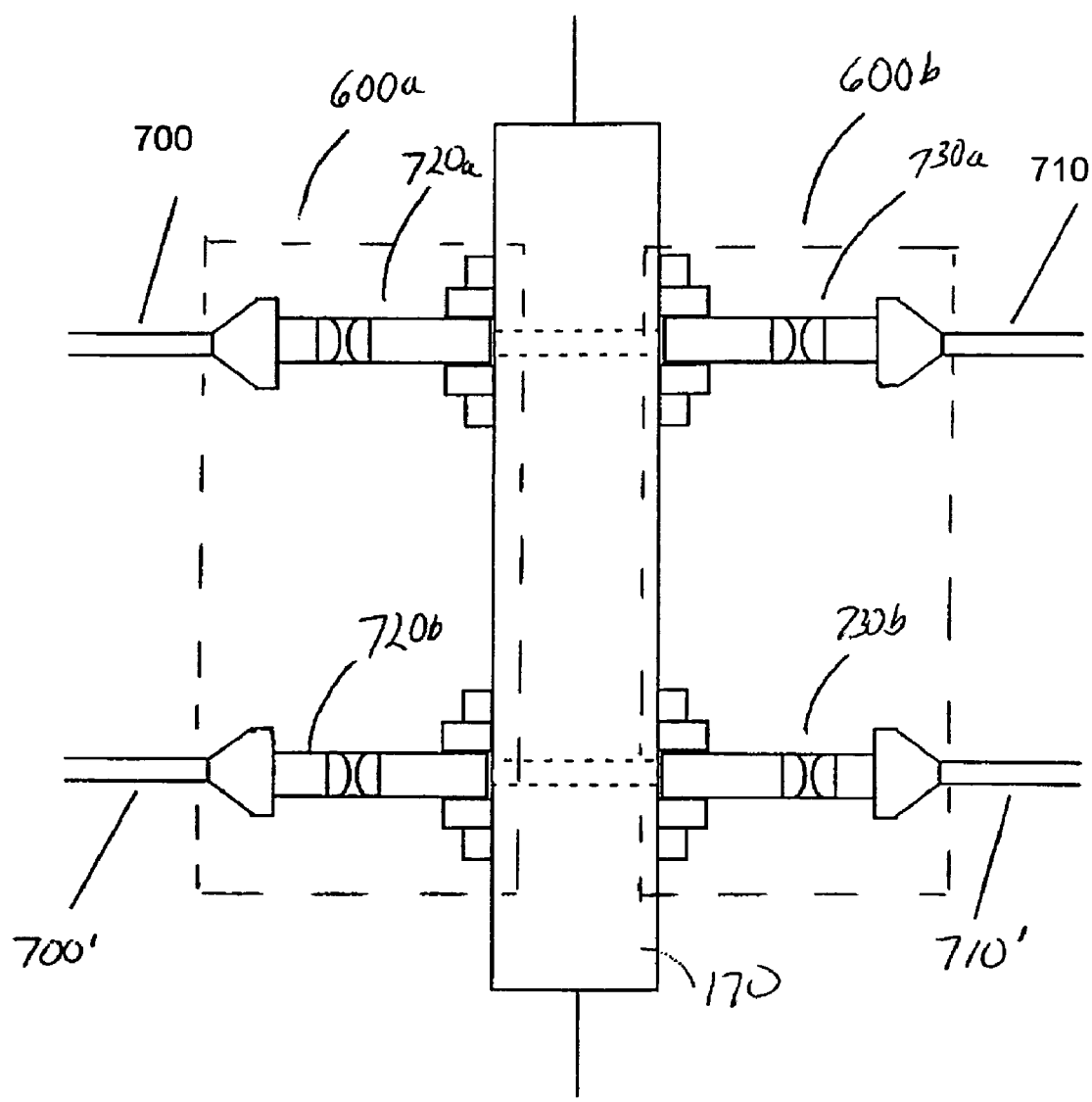
FIG. 3B illustrates an expanded view of one embodiment of the communication system of FIG. 3A.

Another aspect of the present invention is illustrated in FIGS. 3A and 3B. In this embodiment, electromagnetic interference in an MRI procedure is reduced or eliminated through the use of a passive optic communicative coupling (through window 170) of a system controller 100b on the exterior of an imaging room 150 and an injector system (including, for example, an injection control unit 200b and an injection head unit 250b as described above) in the interior of imaging room 150. In that regard, system controller 100b includes a transmitter 332b and a receiver 334b. Transmitter 332b and receiver 333b are preferably connected to a light transmitting or collimating device 600a (for example, one or more lenses) via fiber optic cabling 700 and/or 700'. Light collimating device 600a is aligned with a second light transmitting or collimating device 600b on the interior of imaging room 150 through window 170. Light collimating device 600b is connected to a transmitter 322b and a receiver 324b positioned within injection control unit 200b via fiber optic cabling 710 and/or 710'. By locating transmitter 322b and a receiver 324b within the shielded housing 230b of injection control unit 200b, electromagnetic interference therefrom can be greatly reduced or eliminated.

FIG. 3B illustrates an expanded view of one embodiment of light collimating devices 600a and 600b for communication through window 170. In general, light collimating devices 600a and 600b preferably act to transmit/focus one or more columns or beams of light (for example, visible light such as bright LCD light) for passage through window 170. In the embodiment of FIG. 3B, collimating device 600a includes a first lens assembly 720a and a second lens assembly 720*b*. Lens assembly 720*a* is in communication with transmitter 332*b* via fiber optic cable 700, while lens assembly 720*b* is in communication with receiver 334*b* via fiber optic cable 700'. Collimating device 600*b* includes a third lens assembly 730*a* and a fourth lens assembly 730*b*. Lens assembly 730*a* is in communication with receiver 324*b* via fiber optic cable 710, while lens assembly 730*b* is in communication with transmitter 322*b* via fiber optic cable 710'. In one embodiment, convex lens having a 25 mm diameter and a focal length of 9 mm were used in all lens assemblies 720*a*, 720*b*, 730*a* and 730*b*. Lens assembly 720*a* is aligned with lens assembly 730*a* such that information in the form of a beam of light can be transmitted between transmitter 332*b* and receiver 324*b*. Likewise, Lens assembly 720*b* is aligned with lens assembly 730*b* such that information in the form of a beam of light can be transmitted between transmitter 322*b* and receiver 334*b*. Bi-directional transmission of data can also be achieved using a single lens assembly on each side of window 170 by, for example, multiplexing the transmission of data.

Information can be transmitted via light energy using a protocol such as the Ethernet 10baseT protocol. Examples of transceivers and receivers suitable for use in the present invention include the HFBR 1527 transmitter and the HFBR 2526 receiver available from Hewlett Packard.

Data transmission rates of, for example, 10 Mbps and higher are possible in the embodiment of FIGS. 3A and 3B. Moreover, by positioning transmitter 322*b* and receiver 324*b* (or a transceiver) within shielded housing 230*b* of injection control unit 200*b* and passively transmitting light between collimating devices 600*a* and 600*b*, potentially interfering electromagnetic fields are reduced as compared, for example, to the system of U.S. Pat. No. 5,494,036 in which a transceiver is positioned at the viewing window and connected to the injection control unit thereof via shielded cabling.

Although the present invention has been described in detail in connection with the above embodiments and/or examples, it is to be understood that such detail is solely for that purpose and that variations can be made by those skilled in the art without departing from the invention. The scope of the invention is indicated by the following claims rather than by the foregoing description. All changes and variations which come within the meaning and range of equivalency of the claims are to be embraced within their scope.

What is claimed is:

1. An injector system for injection of a fluid medium into a patient within an electromagnetic isolation area, the injector system comprising:
    (a) a powered injector positioned within the isolation area;
    (b) a first communication unit integral with the powered injector thereby enabling the first communication unit and the powered injector to be moved as a unit;
    (c) a system controller positioned outside the isolation area, the system controller comprising an operator interface;
    (d) a second communication unit integral with the system controller; and
    (e) an intermediate communication unit for ensuring communication between the first and the second communication units and therethrough between the powered injector and the system controller using an authentication technique therewith, the first, the second and the intermediate communication units being adapted to communicate by transmission of radio frequency (RF) energy through the air, the energy being chosen to not create substantial interference with a magnetic resonance imaging scanner.

2. The injector system of claim 1 wherein the RF energy is electromagnetic energy outside the frequency range of the scanner.

3. The injector system of claim 2 wherein the frequency of the RF energy is above approximately 1 Gigahertz.

4. The injector system of claim 1 wherein the intermediate communication unit is positioned within the isolation area.

5. The injector system of claim 1 wherein the injector system has a plurality of the intermediate communication units positioned within the isolation area for ensuring communication between the first and the second communication units and thus the powered injector and the system controller.

6. A system for use with an MRI scanner positioned on a first side of an electromagnetic isolation barrier, the system comprising:
    an injector control unit operable to control injection of a fluid medium into a patient, the injector control unit positioned on the first side of the isolation barrier and comprising a first communication unit integral therewith;
    a system controller positioned on a second side of the isolation barrier, the system controller comprising a second communication unit integral therewith; and
    an intermediate communication unit for ensuring communication between the first and the second communication units and thus the injector control unit and the system controller using an authentication technique therewith, the first communication unit being adapted to communicate with the second communication unit in a bi-directional manner via the intermediate communication unit by transmission of radio frequency (RF) energy through the air, the energy being chosen to not create substantial interference with a magnetic resonance imaging scanner.

7. The system of claim 6 wherein the system has a plurality of the intermediate communication units for ensuring communication between the first and the second communication units and thus the injector control unit and the system controller.

8. The system of claim 6 wherein the RF energy comprises electromagnetic energy outside the frequency range of the scanner.

9. The system of claim 8 wherein the frequency of the RF energy is above approximately 1 Gigahertz.

10. A communication system for use with an MRI imaging system, the communication system comprising:
    a first communication unit positioned on an interior side of the isolation barrier, the first communication unit comprising a first receiver and a first transmitter;
    a second communication unit positioned on an exterior side of the isolation barrier, the second communication unit comprising a second receiver and a second transmitter; and
    an intermediate communication unit for relaying communication between the first and the second communication units, the first communication unit being adapted to communicate with the second communication unit in a bidirectional manner via the intermediate communication unit by transmission of radio frequency (RF) energy through the air using an authentication technique therewith, the energy being chosen to not create substantial interference with the MRI imaging system.

11. The communication system of claim 10 wherein the first communication unit is positioned within a shielded housing.

12. The communication system of claim 10 wherein the first communication unit is positioned within a shielded housing of an injector control unit of an injector system.

13. The communication system of claim 12 wherein the second communication unit is associated with a system controller of the injector system.

14. A method of controlling an injector within an isolation barrier of a magnetic resonance imaging area, the method comprising:
    transmitting RF signals outside the frequency range of the magnetic resonance imaging scanner from a system control unit positioned outside the isolation barrier to an injector control unit inside the isolation barrier, the system control unit comprising an operator interface; and
    transmitting RF signals outside the frequency range of the magnetic resonance imaging scanner from the injector control unit to the system control unit;

wherein RF signals of at least two different frequencies are transmitted to authenticate data, with each of the RF frequencies being outside the frequency range of the scanner.

15. The method of claim 14 wherein a predetermined authentication algorithm is used to authenticate RF signals transmitted between the system control unit and the injector control unit.

* * * * *